(12) United States Patent
Crompvoets et al.

(10) Patent No.: US 8,527,041 B2
(45) Date of Patent: Sep. 3, 2013

(54) SYSTEM, METHOD AND COMPUTER PROGRAM PRODUCT FOR INDICATING STIMULATION SIGNALS TO A USER

(75) Inventors: Floris Maria Hermansz Crompvoets, Eindhoven (NL); Jan Johannes Gerardus De Vries, Eindhoven (NL); Dirk Brokken, Eindhoven (NL); Jacobus Maria Antonius Van Den Eerenbeemd, Eindhoven (NL); Paul Marcel Carl Lemmens, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 80 days.

(21) Appl. No.: 13/203,984

(22) PCT Filed: Feb. 26, 2010

(86) PCT No.: PCT/IB2010/050847
§ 371 (c)(1),
(2), (4) Date: Aug. 31, 2011

(87) PCT Pub. No.: WO2010/100588
PCT Pub. Date: Sep. 10, 2010

(65) Prior Publication Data
US 2011/0306891 A1   Dec. 15, 2011

(30) Foreign Application Priority Data

Mar. 5, 2009  (EP) .................................. 09154451

(51) Int. Cl.
*A61N 1/00*    (2006.01)
(52) U.S. Cl.
USPC .............................. 607/2; 600/509

(58) Field of Classification Search
USPC ..................... 600/508–522, 544, 545; 607/2, 607/58, 62
See application file for complete search history.

(56) References Cited

U.S. PATENT DOCUMENTS

| | | |
|---|---|---|
| 5,267,942 A | 12/1993 | Saperston |
| 2002/0004636 A1 | 1/2002 | Tsubata |
| 2004/0260348 A1 * | 12/2004 | Bakken et al. ................... 607/9 |
| 2005/0240114 A1 | 10/2005 | Elliott |

FOREIGN PATENT DOCUMENTS

| | | |
|---|---|---|
| GB | 2315332 A | 1/1998 |
| WO | 2008110956 A1 | 9/2008 |
| WO | 2009136306 A1 | 11/2009 |

OTHER PUBLICATIONS

Bason et al: "Control of the Heart Rate by External Stimuli"; Nature, Aug. 4, 1972, vol. 238, No. 5362, pp. 279-280.

* cited by examiner

*Primary Examiner* — Scott Getzow

(57) ABSTRACT

Stimulation system for indicating stimulation signals to a user, provided with at least one heart beat sensor for converting measured heart beats into a signal, a processing circuit configured to process the measured heart beat signals, a user interface configured to indicate stimulation signals to a user, wherein the processing circuit is configured to calculate intervals between the detected heart beats and register a predetermined number of successive intervals, predict a time interval between a detected heart beat and a predicted future heart beat based on the registered intervals, and instruct the user interface to indicate a stimulation signal to a user non-simultaneously with the predicted heart beat at the end of the predicted time interval so as to change the heart rate and/or heart coherence of the user.

14 Claims, 3 Drawing Sheets

SYSTEM, METHOD AND COMPUTER PROGRAM PRODUCT FOR INDICATING STIMULATION SIGNALS TO A USER

FIELD OF THE INVENTION

The invention concerns a stimulation system for indicating stimulation signals to a user, provided with at least one heart beat sensor for converting measured heart beats into a signal.

The invention also concerns a method of indicating stimulation signals to a user.

BACKGROUND OF THE INVENTION

Feedback relating to the heart beat or heart rate is oftentimes given to inform a user about his or her physical state. For instance, sportsmen use heart rate information to optimize their performance. The measured heart rate may be presented by certain training devices, so that sportsmen may check to see if their heart rate was within a certain range. The feedback is often given visually, by means of a screen, or audibly. For example, the heart beats may be indicated by visual or audible signs that pulse simultaneous with every heart beat, and/or a sound may be generated when the heart rate exceeds a certain predefined maximum.

SUMMARY OF THE INVENTION

In the published international patent application WO2008/110956 a breathing guidance system is disclosed, wherein the user is guided towards a better heart coherence by giving breathing guidance signals based on the recent heart rate. The system guides the user to breath in sync with the heart beat. By adjusting the breathing to the guidance signals, the user may breathe in sync with the heart beats. The guidance signals are based on the mean of a limited previous number of heart beats. In that way, the user may intuitively reach a better heart coherence by breathing in sync with his heart beats.

It is desirable to influence a user in adapting his or her level of excitement.

A system is provided with a stimulation system for indicating stimulation signals to a user, provided with at least one heart beat sensor for converting measured heart beats into a signal, a processing circuit configured to process the measured heart beat signals, a user interface configured to indicate stimulation signals to a user, wherein the processing circuit is configured to calculate intervals between the detected heart beats and register a predetermined number of successive intervals, predict a time interval between a detected heart beat and a predicted future heart beat based on the registered intervals, and instruct the user interface to indicate a stimulation signal to a user non-simultaneously with the predicted heart beat at the end of the predicted time interval so as to change the heart rate and/or heart coherence of the user.

The heart rate stimulation system may be provided with a heart beat sensor. The heart beat sensor may convert measured heart beats into electrical signals. A processing circuit may be provided to calculate and register heart beat intervals. Based on these registered intervals, a future heart beat interval may be predicted between the last measured heart beat and a next heart beat that is at the end of the predicted interval. A user interface may be provided for indicating stimulation signals non-simultaneously with the predicted heart beat.

The system aims at offering a stimulation signal non-simultaneously, i.e. just before or after, a heartbeat of the user. Since it may not be certain at which exact moment the next heart beat may occur, the stimulation signal is based on a prediction of a future heart beat, and cannot be based on the actual timing of the heart beat.

When the system intends to excite the user, it may offer the stimulation signal just before the predicted future heart beat, and preferably after the heart beat that happened before the actual heart beat corresponding to the predicted next heart beat. When the system intends to relax the user, it may offer the stimulation signal after the predicted next heart beat, and preferably before the second next heart beat. By offering the stimulation signal out of sync with the actual heart beats, the heart rate stimulation system may influence the level of excitement of a user, and therewith change the heart rate of the user, without the user being consciously aware of his or her heart beat and/or of his or her heart coherence. For example, the system may subconsciously guide the user towards heart coherence.

Suppose that a user is relatively excited. Then the user likely has a relatively high heart rate. When a stimulation signal is indicated somewhat earlier than the predicted or actual heart beat, it seemed that this may excite the user even more. On the other hand, when the stimulation signal is indicated slightly later than the actual or the predicted heart beat, this may relax the user.

The system may be well adapted to the momentary personal heart rate condition as it bases its estimation of the future heart beat on a predetermined number of the last measured heart beats. In an embodiment, the predetermined number of registered intervals is two hundred or less, preferably hundred or less, more preferably of fifty or less. In a specific embodiment, the system predicts the timing of the future heart based on approximately the last twenty or less detected heart beats.

The prediction may be based on an expectation, or estimation, of when the next heart beat will occur. The processing circuit may be configured to predict the coming time interval between a last heart beat and a future heart beat by probability analyzing the registered intervals. This has shown to give relatively good results of predicting the heart beat. In a preferred embodiment, a histogram of the registered intervals is made. Based on this histogram a future heart beat interval can be predicted. In another embodiment, the prediction of the future heart beat may be based on the mean of a registered sequence of heart beats, for example the mean of the last five to fifteen registered heart beats.

If a predetermined number of heart beat intervals is registered and plotted in the histogram, ranges of heart beat intervals can be plotted in the histogram according to their percentile. By using a histogram, the timing of the stimulation signals may be given in a relatively controlled and effective manner, also when the heart rate is relatively irregular. In an embodiment, the predicted time interval may be based on the median, i.e. a percentile of 50, or an approximation thereof. A percentile of 50 may give the largest chance that the timing of the predicted heart beat is indeed equal or approximately equal to the timing of the corresponding actual heart beat.

The stimulation signal may be indicated to the user before or after the time interval corresponding to the median has passed. In the histogram, the intervals corresponding to a percentile of 0-50 will have an equal duration as, or lower duration than, the median of the histogram, and the intervals corresponding to percentiles of 50-100 will have an equal duration as, or higher duration than the median of the histogram.

The percentiles that are lower than 50 may refer to heart beat intervals of relatively short duration. Indicating a stimulation signal at the end of a time interval corresponding to a percentile that is lower than 50, may give a relatively high chance that the stimulation signal is earlier than the actual heart beat. The percentiles higher than 50 may refer to relatively heart beat intervals of relatively long duration. Indicating a stimulation signal at the end of a time interval corresponding to a percentile that is higher than 50, may give a relatively high chance that the stimulation signal is later than the actual heart beat.

The processing circuit may be configured to instruct the user interface to indicate the stimulation signal at a second predetermined percentile of the histogram that is different from the predetermined percentile corresponding to the predicted future heart beat interval. The chosen percentile may be predetermined according to a level of exciting or relaxing the user, based on the detected intervals. In an embodiment, the stimulation signal may be indicated at an interval corresponding to a percentile that is different than 50. For example, to excite the user, the second predetermined percentile may be lower than the median, for example between 0 and 49. To relax the user, the stimulation signal may be indicated corresponding to a percentile that is higher than the median, for example between 51 and 100.

In practice, the stimulation signal frequency may be lower than the heart rate, so that stimulation signals may be indicated before or after every predetermined number or cycle of heart beats. One cycle of heart beats may relate to breathing in and out one time. For example, after every $6^{th}$, $7^{th}$, $8^{th}$, or $9^{th}$ predicted future heart beat a signal may be indicated, or after every $6^{th}$, $7^{th}$, $8^{th}$, or $9^{th}$ heart beat a future heart beat may be predicted and the signal may then be indicated just before or after that predicted heart beat.

In a coherent state, the registered heart beat intervals may be plotted in relation to time according to a repetitive pattern. In a coherent state, a person may have a regular breathing pattern, and a repetitive heart beat interval pattern that corresponds to that breathing pattern. Mostly, the heart beat intervals show a sinusoid pattern in relation to time, wherein the frequency of the sinusoid corresponds to the breathing frequency. When such repetitive pattern is recognized this may indicate that a heart coherence is present. A next heart beat may be predicted according to such repetitive pattern. Therefore, if such repetitive pattern can be extracted from the plot of the registered intervals, a future heart beat interval may be based on further repetition of the repetitive pattern.

In an embodiment, if the registered intervals are plotted in relation to time, the repetitive pattern may a sinusoid. A sinusoid may represent a coherent heart rate. In such case, the future heart beat may be predicted to lie on a further continuance of the sinusoid.

The system may on the one hand use a histogram of registered heart beat intervals to predict a future heart beat interval, and on the other hand uses a detected repetitive pattern, that is detected from the series of registered intervals, to predict a future heart beat interval. The processing circuit may be configured to detect whether coherence is present by detecting whether a certain repetitive pattern, preferably a sinusoid, is present in a plot of the registered intervals in relation to time. If no coherence is detected, the system may predict the next heart beat interval based on a certain percentile of the histogram. If coherence is detected, the system may predict the next heart beat interval based on the repetitive pattern, preferably by making the pattern repeat in the future.

In a further embodiment, the stimulation signals may comprise a tactile stimulation, such as a vibration. This may increase the level of intuitive adjustment the heart rate in relation to the stimulation signals. The user interface may comprise a tactile stimulator to indicate the stimulation signals to the user. The user interface may comprise flexible material that can be worn on a user's body for directly stimulating the body of the user.

In a third aspect above mentioned goal and/or other goals may be achieved by a method according to claim 13.

In a fourth aspect above mentioned goal and/or other goals may be achieved by a computer program product according to claim 14.

BRIEF DESCRIPTION OF THE FIGURES

Further embodiments of the invention and advantages thereof may be set out in the claims and description, with reference to the drawings.

In the drawings.

DETAILED DESCRIPTION OF EMBODIMENTS

Figure 1:
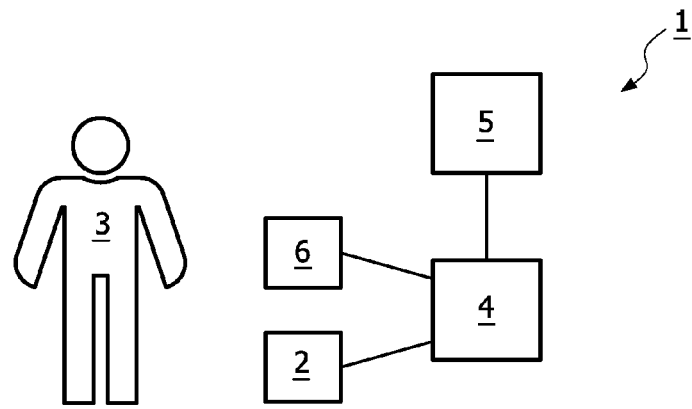
FIG. 1 schematically shows a diagram of a heart rate stimulation system.

In this description, identical or corresponding areas have identical or corresponding reference numerals. The exemplary embodiments shown should not be construed to be limitative in any manner and serve merely as illustration.

In this description, excitement may be understood as arousal. An opposite term for excitement may be relaxation. The system described herein may adjust the excitement, arousal, relaxation and/or heart rate of the user.

In FIG. 1 a schematic diagram is shown of a heart rate stimulation system 1. The system 1 comprises heart beat sensors 2 that are arranged to convert measured heartbeats from a user 3 into a signal. The heart beat sensors 2 may be attached close to, or against the body of the user 3. A processing circuit 4 may be provided that is arranged to process the heart beat signals. The processing circuit 4 may calculate heart beat time intervals between detected heart beats and register the calculated intervals on a digital storage arrangement 5. The processing circuit 4 may further be arranged to instruct a user interface 6 to signal stimulation signals to the user 3. The user interface 6 may be attached to the body of the user 3, for example in a similar manner as the heart beat sensors 2.

The digital storage arrangement 5 for storing registered heart beat time intervals may comprise any known digital storage arrangement 5 such as a volatile or non-volatile memory, for example a hard disk.

The heart beat sensor 2 may comprise any known device for converting heart beat signals into electrical signals. The heart beat sensor 2 may for example be arranged to detect heart beats via selectively placed electrodes on the skin of the user 3, via an electrocardiogram, or a blood pulse meter, or for example by a plethysmograph for example using a photodiode or impedance measuring technique. The heart beat sensor 2 may be provided, and/or integrated in a patch and/or clothing. The heart rate sensor 2 may be provided in flexible material that can be worn on, or near, the user's body.

Figure 2:
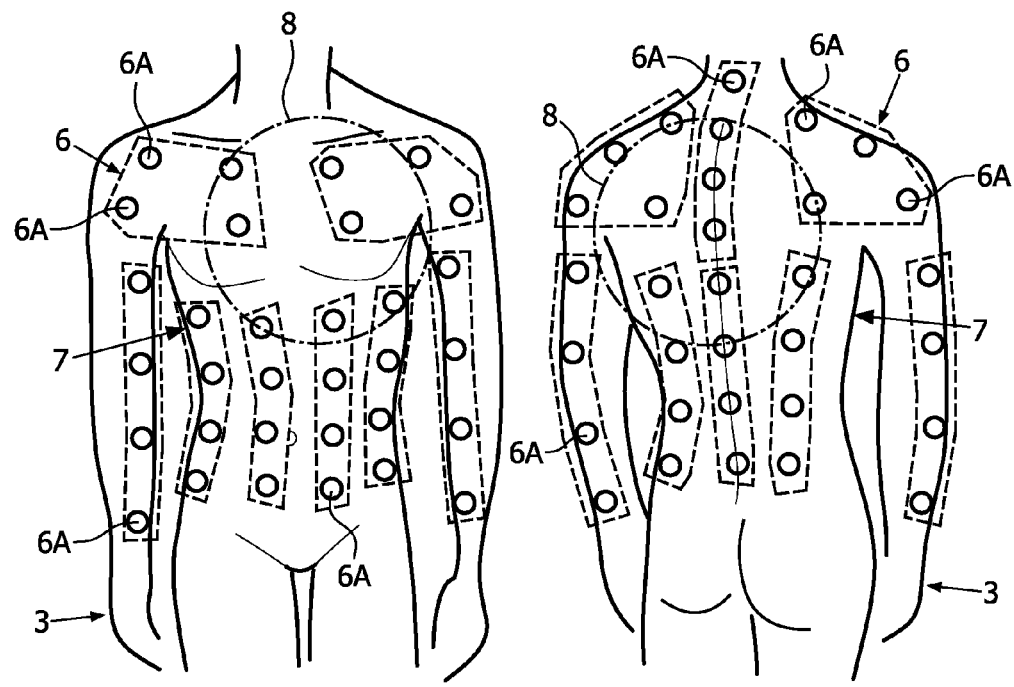
FIG. 2 schematically shows a front view and a rear view, on the left and right, respectively, of a user interface on a user's body.

Preferably, the user interface 6 comprises at least one, preferably multiple tactile stimulators 6A, as is illustrated in FIG. 2. The tactile stimulators 6A may be arranged to indicate tactile stimulation signals to the user 3, for example in the form of vibrations. The user 3 may sense such signal and may become more excited or more relaxed, depending on the timing of the stimulation.

The tactile stimulator 6A may be arranged to provide electrical and/or mechanical signals, for example shocks. The tactile stimulator 6A may be arranged to provide one, or a small amount of movements corresponding to one stimulation signal. The tactile stimulator 6A may be arranged to vibrate such that it can be sensed by a user. A vibration may comprise movements of a relatively high frequency. For example metal or plastic part may be provided against and/or near the body of a user 3. During the stimulation signal, the metal or plastic part may vibrate with respect to the body.

The user interface 6 may be provided, and/or integrated in a patch and/or clothing. The user interface 6 may be provided in flexible material that can be worn on, or near, the user's body for directly stimulating the body of the user, as is shown in FIG. 2. In these cases, the user interface 6 preferably comprises a tactile stimulator 6A. Both the sensors 2 and the user interface 6 may be part of the same device, for example part of clothing and/or a patch.

In an embodiment, as depicted in FIG. 2, the user 3 may wear the tactile stimulator 6A and/or the sensor 2 in a vest, jacket and/or patch. The tactile stimulator 6A may comprise a vibrotactile actuator. Preferably, the tactile stimulator 6A is arranged to be placed at or near the torso of a user 3. It may be convenient, if the tactile stimulator 6A and/or the sensor 2 would be provided in a pad that can be integrated with clothing such as a jacket, coat, sweater, sports clothing such as sweat absorbing underwear, a chest belt, or the like, such that the heart rate stimulation system may be relatively non-obtrusive. In an embodiment, the heart rate stimulation system 1 comprises a chest belt with integrated electrocardiagram-pads and a tactile stimulator 6A.

In FIG. 2 multiple tactile stimulators 6A are shown that are worn near the torso 7 of a user 3. The circle indicates a heart region 8. It may be beneficial if the stimulators 6A are arranged near the torso 7 of a user 3. It may be specifically beneficial if the stimulators 6A are arranged near the heart region 8 of the user 3. A user 3 may then correlate a received signal with his or her heart beat. It was found that by offering a vibration during a relatively short time period, e.g. of less than a second, just before every nth heart beat, wherein n may represent a number of heart beats in one breathing cycle, this may excite the user 3 subconsciously.

In further embodiments, the user interface 6 may provide other stimulation signals. For example, the user interface 6 may comprise an audio device for providing audible stimulation signals, or a visual screen device for providing visual stimulation signals.

The heart rate stimulation system 1 may indicate stimulation signals through the user interface 6. The system 1 may be arranged to stimulate the user 3 to reach a heart rate that is coherent with the breathing. When the frequency of the heart beats is regular, a future heart beat may be predicted by extrapolating the detected signals. However, in most cases, the heart rate does not precisely follow a regular pattern, but may be rather irregular. Therefore, the timing of the future heart beat may be rather unpredictable.

Figure 3:
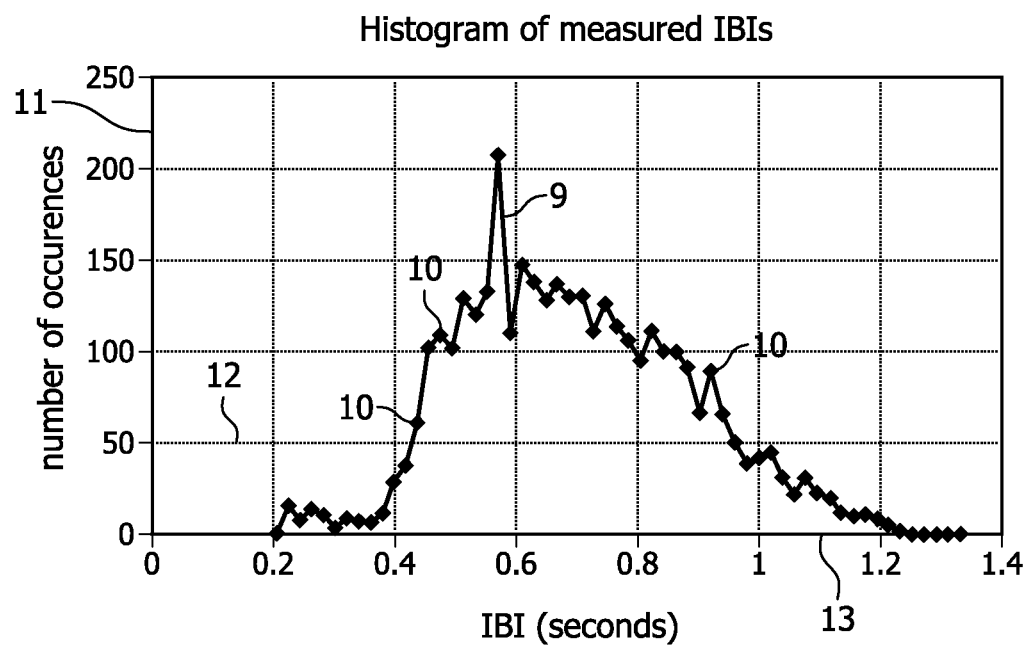
FIG. 3 shows a histogram of detected heart beat intervals.

In FIG. 3 a histogram 9 of heart beat intervals 10 is plotted according to a detected sequence of heart beats. The vertical axis 11 represents a detected number of occurrences of the respective intervals 10. The vertical axis 11 is divided in steps 12 of fifty. The horizontal axis 13 represents the durations of the respective intervals 10, wherein the respective intervals 10 may be rounded up or down, for example to the nearest two hundredths of seconds. The intervals 10 may be plotted every two hundredths of seconds. For the purpose of illustration, the histogram has plotted a relatively large number of heart beat intervals 10 of a user 3.

The heart beat intervals may be modeled as a stochastic variable. Its probability distribution may be approximated by a histogram of previous recorded heart beat intervals. Predicting the next heart beat interval can be achieved by drawing an instance from this stochastic variable.

The shown histogram 9 relates to a relatively high amount of detected heart beats. In practice, the system 1 may use histograms 9 that have a smaller number of detected heart beat intervals 10. By considering only the most recently detected heart beat intervals 10 in the histogram 9, temporary changes in the main level and/or the median of the heart beat intervals, by for example temporary changes in intensity of certain activities and/or temporary changes in excitement, may be taken into account. In an embodiment, the number of registered intervals in the histogram may be two hundred or less, preferably hundred or less, more preferably of fifty or less. In a specific embodiment, the system predicts the timing of the future heart based on approximately the last twenty or less detected heart beat intervals.

By choosing the n-th percentile of this histogram, there is a probability of 100−n percent that the corresponding predicted value is smaller than the actual heart beat value, and a probability of n percent that the predicted value is larger than the actual value. For example, if n=10 is chosen as limit than the chance of stimulating sooner than the actual heart beat, i.e. that the predicted value is smaller than the actual heart beat, is approximately 90%.

Using this approach, n=50 may give the largest chance of predicting the next heart beat interval correctly. For regular stimulation, aimed at providing stimulation signals in sync with the actual heart beat, the stimulation signal would be indicated in sync with the predicted heart beat, which would be at the end of the interval corresponding to n=50.

However, next to providing said regular stimulation, the system 1 may be configured to excite or relax the user 3. For example, to excite a user 3, the system 1 may aim to provide stimulation earlier than the actual heart beat. Therefore, the interval between a lastly measured heart beat and a predicted future heart beat may be chosen to be amongst the lower percentiles of the histogram, that is, a percentile below 50, or even below the lowest measured heart beat interval. For example, an interval corresponding to a percentile of 10 (n=10) may be chosen. On the other hand the system 1 may aim to relax a user 3, for which intervals corresponding to percentiles higher than 50 may be chosen, such as for example corresponding to approximately 80 or 90. These percentiles may be predetermined, based on the distribution in the histogram, and based on the level of excitement and/or relaxation that is aimed at.

Figure 4:
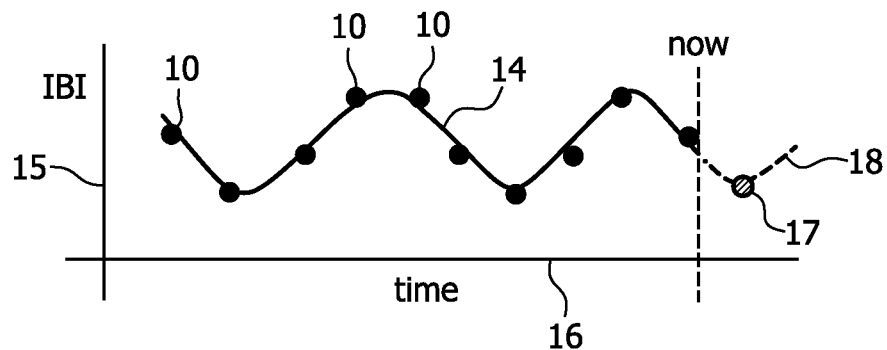
FIG. 4 shows a sinusoid pattern of detected heart beat intervals.
Figure 5:
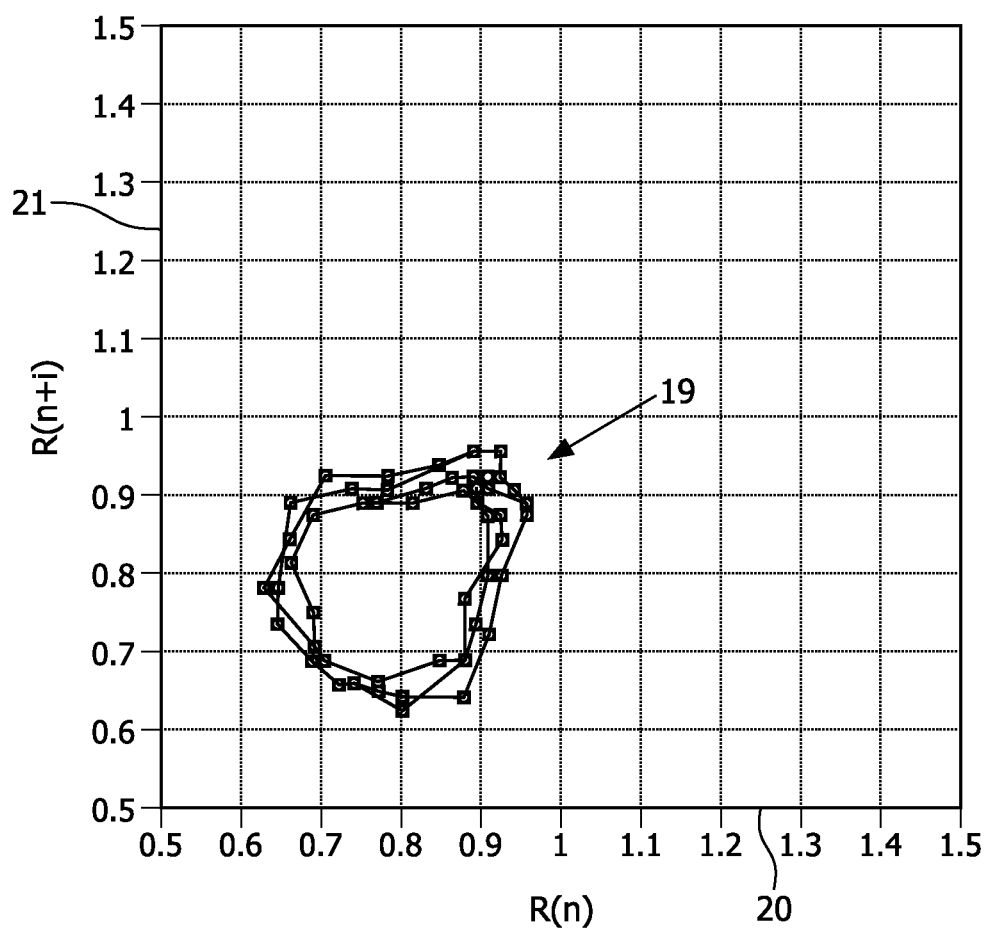
FIG. 5 shows a graph that is obtained by applying a Poincaré method to detected heart beat intervals.

When a user 3 is in a coherent state, his heart rate and breathing pattern may be synchronized. In such a coherent state, the user 3 may for example be in a both focused and relaxed condition. During a coherent state, the heart beat intervals and breathing frequency may be plotted in relation to time in a repetitive pattern, and the plots may be related to each other. As shown in FIG. 4, when plotted in relation to time, the heart beat intervals 10 may show a pattern that corresponds to a sinusoid, wherein each peak may relate to a breathing cycle. For example, a generic model (a*sin(b*x+c)+d) of a sinusoid 14 may be fit to the plotted detected intervals 10, for example by using a least squares method for fitting a curve 14 between the measured intervals 10.

In FIG. 4, the vertical axis 15 indicates a respective heart beat interval value, and the horizontal axis 16 corresponds to time. As shown, the heart beat intervals 10 that are plotted in relation to time can be plotted along a sinusoid 14. This sinusoid pattern 14 may be explained by the fact that the heart rate momentarily increases and decreases, when a person breaths in and breaths out, respectively.

The sinusoid 14 may be used to extrapolate the heart beat interval pattern, to predict one or more future heart beats 17 along a continuance 18 of the sinusoid (dotted line in FIG. 4). In this way, the coherent pattern may be optimally used to predict the next heart beat with a relatively high precision.

Several methods may be used, by itself or in combination, to distinguish a coherent state of a user. One method is to use a least squares fit method to check if the detected intervals fit a sinusoid 14. If the fit is very bad, i.e. there is a high sum of squared differences between the extrapolated curve and the detected intervals, a person may not be in a coherent state. In this case, the future heart beat interval may for example be predicted by using the histogram method, as explained above.

Another method may be to apply a Fourier transformation to the detected interval values, as known in the art. The outcome of the Fourier transformation may be plotted in a graph, wherein a sinusoid pattern may be represented by relatively sharp peaks in the graph. A way to determine a coherent state may be to verify whether a relatively sharp peak is present around a typical breathing frequency of a person, for example at approximately 0.1 Hz. If no coherent state is detected using this method, the future heart beat interval may for example be predicted by using the histogram method as described above.

Another method to extrapolate a coherent state may be to use a Poincaré method. This method is inter alia discussed in European patent application No. 08155890.0, filed on May 8, 2008 (or any patent application claiming its priority). In this method a graph 19 may be plotted wherein the nth measured interval is plotted on the x-axis 20, versus the n+ith measured interval on the y-axis 21, wherein i represents the ith measured cycle. This may results in an ellipse or circle, as shown in the graph 19. An opener and thinner ellipse may represent a more "coherent state", i.e. relatively good syncing between breathing pace and heart rate. The radius or size of the ellipse may be a measure for the amplitude of the heart rate variability. The thickness of the line of the ellipse, i.e. the variation in radius, may be a measure for the coherence. For further explanation, please be referred to above mentioned European patent application No. 08155890.0.

Using the Poincaré method a coherent state of the user 3 may be determined. If no coherent state seems to be present, the system 1 may refer to using the histogram 9, as described above.

When a future heart beat is predicted based by extrapolating the detected intervals with any of above discussed methods, the stimulation signal may be indicated before or after the predicted heart beat for exciting or relaxing the user 3. By using the histogram a relatively controlled way for exciting or relaxing can be applied, even when no particular pattern or regularity is present in the detected intervals plotted in relation to time. In another embodiment, the predicted future heart beat interval may for example be based on the mean of a sequence of previous measured heart beat intervals, preferably a relatively short number of intervals.

The system 1 may be employed in for example clothing or body patches that may influence the physiological condition of the user 3. It may be applied in optimal performance indicators for sportsmen. It may be employed in so-called tactile clothing that may relax and/or energize its users 3. These types of stimulators may be perceived as relatively non-intrusive, and may influence the user 3 subconsciously.

The methods described above may be applied by processing signals that are received from the heart beat sensors 2. A computer program product, e.g. stored on a device, storage arrangement 5 and/or network, may be used to instruct the processing circuit 4. The system 1 may comprise a device that is completely integrated, for example in clothing, or may be modularly built, wherein certain parts may be connected via networks.

It shall be obvious that the invention is not limited in any way to the embodiments that are represented in the description and the drawings. Many variations and combinations are possible within the framework of the invention as outlined by the claims. Combinations of one or more aspects of the embodiments or combinations of different embodiments are possible within the framework of the invention. All comparable variations are understood to fall within the framework of the invention as outlined by the claims.

The invention claimed is:

1. A stimulation system for indicating stimulation signals to a user, comprising:
   at least one heart beat sensor for converting measured heart beats into a signal;
   a processing circuit configured to process the measured heart beat signals; and
   a user interface configured to indicate stimulation signals to a user;
   wherein the processing circuit is configured to:
   calculate time intervals between detected heart beats and register a predetermined number of successive calculated heart beat time intervals,
   predict a heart beat time interval (a) between (a)(i) a detected heart beat and (a)(ii) a predicted future heart beat, (b) wherein the predicted heart beat time interval is based on the registered predetermined number of successive calculated heart beat time intervals, and
   instruct the user interface to indicate a stimulation signal to a user non-simultaneously with the predicted future heart beat at the end of the predicted heart beat time interval so as to change the heart rate and/or heart coherence of the user, wherein (i) to excite the user, the processing circuit instructs the user interface to indicate the stimulation signal just before the predicted future heart beat, and after a heart beat that occurs before an actual heart beat corresponding to the predicted future heart beat, and (ii) to relax the user, the processing circuit instructs the user interface to indicate the stimulation signal after the actual heart beat corresponding to the predicted future heart beat, and before a second future heart beat.

2. The stimulation system according to claim 1, wherein the processing circuit is configured to calculate the predicted heart beat time interval by modeling the registered predetermined number of successive calculated heart beat time intervals as a stochastic variable.

3. The stimulation system according to claim 1, wherein the processing circuit is configured to calculate a histogram of the registered predetermined number of successive calculated heart beat time intervals, and to predict a heart beat interval based on a predetermined percentile of the histogram.

4. The stimulation system according to claim 1, wherein the predicted time interval is based on a median of the registered predetermined number of successive calculated heart beat time intervals.

5. The stimulation system according to claim 3, wherein the processing circuit is configured to instruct the user interface to indicate the stimulation signal at a second predetermined percentile of the histogram that is different from the predetermined percentile corresponding to the predicted heart beat interval.

6. The stimulation system according to claim 5, wherein to excite the user, the second predetermined percentile is lower than a median of the registered predetermined number of successive calculated heart beat time intervals, and wherein to relax the user, the stimulation signal is further indicated corresponding to a percentile that is higher than the median.

7. The stimulation system according to claim 1, wherein the predetermined number of successive calculated heart beat time intervals of the registered intervals comprise one selected from the group consisting of (i) two hundred or less, (ii) one hundred or less, and (iii) fifty or less.

8. The stimulation system according to claim 1, wherein the processing circuit is further configured to:
   plot the registered predetermined number of successive calculated heart beat time intervals in relation to time,
   verify if a repetitive pattern can be extracted from the plot of the registered intervals, and,
   if the repetitive pattern can be extracted, then predict the future heart beat interval based on further repetition of the repetitive pattern.

9. The stimulation system according to claim 8, wherein the repetitive pattern comprises a sinusoid, representing a coherent heart rate, wherein the predicted future heart beat lies on a further repetition of the sinusoid in relation to time.

10. The stimulation system according to claim 1, wherein the processing circuit is further configured to:
   detect whether a repetitive pattern relating to heart coherence is present in the registered predetermined number of successive calculated heart beat time intervals in relation to time, and
   (i) predict the next heart beat interval based on a percentile of a histogram of the registered predetermined number of successive calculated heart beat time intervals, when no heart coherence is present, and (ii) predict the next heart beat interval based on the repetitive pattern corresponding to the heart coherence, when heart coherence is present.

11. The stimulation system according to claim 1, wherein the user interface comprises a tactile stimulator to indicate the stimulation signals to the user.

12. The stimulation system according to claim 11, wherein the user interface comprises flexible material that can be worn on or near a user's body for directly stimulating the user's body.

13. A method of indicating stimulation signals to a user comprising:
   detecting, via at least one heart rate sensor, a sequence of heart beats;
   calculating, via a processing circuit, intervals between the detected heart beats and registering, via the processing circuit, a predetermined number of successive calculated heart beat time intervals;
   predicting, via the processing circuit, a time interval (a) between (a)(i) a detected heart beat and (a)(ii) a predicted future heart beat, (b) wherein the predicted future heart beat time interval is based on a sequence of the predetermined number of successive calculated heart beat time intervals of the registered intervals; and
   indicating, via a user interface, a stimulation signal to a user non-simultaneously with the predicted heart beat so as to change a heart rate and/or heart coherence of the user, wherein (i) to excite the user, the processing circuit instructs the user interface to indicate the stimulation signal just before the predicted future heart beat, and after a heart beat that occurs before an actual heart beat corresponding to the predicted future heart beat, and (ii) to relax the user, the processing circuit instructs the user interface to indicate the stimulation signal after the actual heart beat corresponding to the predicted future heart beat, and before a second future heart beat.

14. A non-transitory computer-readable medium embodied with a computer program for indicating simulation signals to a user, which when executed on a computer controls the computer to
   detect a sequence of heart beats via heart beat sensors,
   calculate intervals between the detected heart beats and register a predetermined number of successive calculated heart beat time intervals,
   predict a time interval (a) between (a)(i) a detected heart beat and (a)(ii) a predicted future heart beat, (b) wherein the predicted future heart beat is based on a sequence of the predetermined number of successive calculated heart beat intervals of the registered intervals, and
   indicate a stimulation signal via a user interface, non-simultaneously with the predicted future heart beat so as to change a heart rate and/or heart coherence of the user, wherein (i) to excite the user, instruct the user interface to indicate the stimulation signal just before the predicted future heart beat, and after a heart beat that occurs before an actual heart beat corresponding to the predicted future heart beat, and (ii) to relax the user, instruct the user interface to indicate the stimulation signal after the actual heart beat corresponding to the predicted future heart beat, and before a second future heart beat.

* * * * *